United States Patent [19]
Atkinson

[11] Patent Number: 5,808,118
[45] Date of Patent: Sep. 15, 1998

[54] SURFACE TREATMENTS FOR TITANIUM DIOXIDE AND OTHER INDUSTRIAL PIGMENTS

[76] Inventor: George Kimball Atkinson, 1820 N. Seventh Ave., Laurel, Miss. 39440

[21] Appl. No.: 810,125

[22] Filed: Feb. 25, 1997

[51] Int. Cl.⁶ .................................................. C07C 311/05
[52] U.S. Cl. ................................ 554/46; 554/47; 554/48; 554/54; 252/355; 106/493
[58] Field of Search ................................ 554/46, 47, 48, 554/54; 252/355

[56] References Cited

U.S. PATENT DOCUMENTS 2,329,086  9/1943  Roninson .................................. 554/46
3,438,898  4/1969  Schlobohm et al. ..................... 554/48

*Primary Examiner*—Richard L. Raymond
*Attorney, Agent, or Firm*—Herbert M. Hanegan

[57] ABSTRACT

A pigment additive for improved dispersibility and reduction of photodegradation.

21 Claims, No Drawings

SURFACE TREATMENTS FOR TITANIUM DIOXIDE AND OTHER INDUSTRIAL PIGMENTS

This invention relates to surfactant treated particulate titanium dioxide and other pigments. More particularly, this invention is concerned with surfactant treated titanium dioxide and other particulate materials readily employable in coating compositions, plastic molding compositions, reinforced plastic composite compositions, and paper making compositions.

Industrial pigment particles agglomerate or cake together into hard packed clusters during the drying operation near the end of the manufacturing process. Forces holding pigment clusters together are not large in many cases but are yet large enough that the pigment user, those who incorporate industrial pigments into their products such as paints and plastics and the like, are required to subject industrial pigments to a milling operation in which the agglomerates are sheared under stress into particles of suitable smallness and homogenized into the matrix or product which incorporates them. The process is dispersion.

Pigment dispersion is a bottleneck, a limiting requirement, and the most expensive operation in terms of energy and time in manufacturing processes which employ pigments. This present invention is concerned with the employment of surfactants for the surface treatment of pigments during the pigment manufacturing process in order to provide pigments of improved dispersibility in subsequent manufacturing processes and in some cases, to provide improvements in certain important aspects of products incorporating these surface treated pigments.

Titanium dioxide pigments present a special case. Uncoated titania pigments are extremely difficult to disperse. In addition, their employment in pigmented plastics, coatings, papers, and fiber compositions induces a photoactivity which results in oxidative degradation which is destructive of the materials of which they are a part. As a consequence, most titanium dioxide pigments are provided with some form of surface coating during manufacture to promote dispersibilty and to reduce photoactivity. Two materials in widespread use at present are silica and alumina. These materials are coated onto the surfaces of pigment particles in the range of three to ten percent by weight of $TiO_2$.

The surface treatment of pigments can provide the following beneficial primary effects:

1. The total number of agglomerates is reduced.
2. Any agglomerates that are present are more easily broken up since their mechanical strength is reduced.
3. Pigment particle wettability is improved due to a lowering of the interfacial tension between the pigment surface and the application medium.
4. Wettability of the pigment particles is also improved due to the liberation of the free energy of solution of the coating agent on the pigment surface. (Surface Treatment of Organic Pigments; K. Merkle and H. Schafer; *Pigment Handbook*, page 158, Vol. III; John Wiley and Sons, Inc., 1973.)

Pigments, their preparation and properties are described in volumes I, II and III of the book "Pigment Handbook" published by John Wiley & Sons, Inc. The uses, preparation and characterization of pigments is further described in the various units of "The Federation Series on Coating Technology" published by the Federation of Societies for Coating Technology.

German Pat. Nos. 889,042 and 930, 998 teach the use of surface-active substances as emulsifiers together with oils in the manufacture of water-insoluble azo-dyestuffs having a soft grain.

U.S. Pat. No. 3,120,508 discloses that water-insoluble azo-dyestuffs having a particularly high tinctorial strength can be prepared by adding during the coupling cationic surface-active compounds without simultaneously using oils.

U.S. Pat. No. 3,437,502 teaches improvement of opacity and dispersibility of titanium dioxide through surface treatment with silica and alumina. U.S. Pat. No. 3,658,566 teaches the production of titanium dioxide of improved properties by treatment with oxides of silicon and aluminum. U.S. Pat. No. 4,599,114 discloses improvement of pigmentary properties for a variety of pigments through surface treatment of pigment filter cakes.

Cationic surface-active compounds are described in the book "Surface-Active Agents and Detergents" by A. M. Schwartz, J. W. Perry and J. Berch, vol. II (1958), pages 103 to 119.

U.S. Pat. Nos. 4,599,114, 4,471,780 and 4,909,852 disclose compositions having surfactants consisting of the reaction product of a diamine, a carboxylic acid and a fatty acid.

Suitable cationic surface-active substances are, for example, long-chained aliphatic amino compounds that contain about 10 to 18 carbon atoms, or the salts of such nitrogen compounds with carboxylic acids, such for example, as formic acid, acetic acid, oleic acid, tallow fatty acid, lactic acid or mineral acids, for example, hydrochloric acid. Fatty amines are for example, coconut oil amine, oleyl amine, stearyl amine, and tallow fat amine, as well as the secondary and tertiary amines or quaternary ammonium compounds derived therefrom that may carry as substituents aliphatic, aromatic or oxethylated radicals, for example, alkyldimethyloxyethyl ammonium chloride. Oxethylated fatty amines in their secondary, tertiary or quaternary form are also suitable. Also useful are the condensation products of long-chained, in some cases also unsaturated, carboxylic acids with amines, in particular alkylenediamines, alkylenetriamines, or alkylenepolyamines containing alkylene radicals of low molecular weight, for example, ethylene diamine, diethylene triamine, etc., as well as the secondary, tertiary or quaternary amines formed by alkylation of the condensation products, especially in the form of their water-soluble salts with the above-mentioned acids. Further, there may be used fatty acid amides and esters of long-chained carboxylic acids with alkylol amines, for example, triethanolaminoleate, stearate, and the like, further also cyclical, nitrogen-containing compounds, for example, long-chained derivatives of morpholine, imidazoline, piperidine, piperazine or pyridine. The above-mentioned amino compounds are used preferably in the form of their carboxylic or hydrochloric salts.

British Patent No. 1,080,115 discloses the use of primary long chain alkyl amines for treating pigments improving their dispersibility.

There is described herein the use of surfactants which have the capability of increasing the dispersibility of titanium dioxide and other pigments to which they are applied. In conjunction with improved dispersibility, the surfactants also have the capability to reduce the photoactivity of titanium dioxide pigments which have been incorporated into a matrix and exposed to radiation as already described. In this usage the surfactants are applied to titanium dioxide pigments which have received no previous surface treatment.

Titanium dioxide is an established pigmentary material which can also be employed as a reinforcing filler, albeit an expensive one. It is commonly made by two processes, the chloride process and the sulfate process. The chloride process is dry process wherein $TiCl_4$ is oxidized to $TiO_2$ particles. In the sulfate process titanium sulfate, in solution, is converted by a metathesis reaction to insoluble and particulate titanium dioxide. In both processes, particle formation can be seeded by aluminum compounds. Thereafter, the processes are essentially the same. The $TiO_2$ particles in a water slurry are put through multiple hydroseparations to separate out the large particles and the further refined pigment in slurry form is passed to a treating tank where the particles may be treated with an aluminum compound and/or silicon compound, such as aluminum triethoxide, sodium aluminate, aluminum trichloride, aluminum sulfate, ethyl silicate, sodium silicate, silicon tetrachloride, trichlorosilane, and the like. By pH adjustment, the pigment is flocculated and precipitated with its coating of alumina and/or silica, or without any coating. It is then made into a filter cake by a vacuum drying and further dried in an oven, generally of a vibrating type. The optimum average particle size can range from about 0.05 to about 0.35 microns with a range of about 0.1 to about 0.25 more preferable.

One feature of the dispersion promoters of this invention is that they alter the surface characteristics of the titanium dioxide or other pigments so that it is more readily and more thoroughly dispersed within the resin or plastic in which it is incorporated, and this serves to enhance the appearance of the resulting composite and increase the overall strength of the composite when the particulate material employed is one which serves to reinforce the plastic or resin.

The amount of dispersion promoter provided upon the titanium dioxide particles, as characterized herein, is that amount which alters the surface characteristics of the particles so that they are more readily dispersed within the resin, plastic, paper making composition or other medium in which they are incorporated. Typically, the amount of the dispersion promoter which is supplied to the titanium dioxide may be from as little as about 0.25 weight percent to about 5 weight percent, based upon the weight of the titanium dioxide particles. As a rule, about 0.5 to about 3 weight percent of the dispersion promoter and/or its derivatives is adequate for the purposes of appropriately altering the surface characteristic of the particles. Most preferred is 2%. Preferred is 2% or less weight percent for titanium dioxide and inorganic color pigments, 1% or less weight percent for inert pigments, and much higher amounts for the organic and carbon black pigments which have very high surface areas. For some pigment and mediums the amount of dispersion promoter may be from about 1.00 to about 15.0 percent or higher.

The amount of dispersion promoter provided when used with carbon black particles, as characterized herein, is that amount which alters the surface characteristics of the particles so that they are more readily dispersed within the resin, plastic, paper making composition or other medium in which they are incorporated. Typically, the amount of the dispersion promoter which is supplied to the carbon black may be from as little as about 1.00 weight percent to about 15.0 weight percent, based upon the weight of the carbon black particles. As a rule, about 4.0 to about 10.0 weight percent of the dispersion promoter and/or its derivatives is adequate for the purposes of appropriately altering the surface characteristic of the particles. Most preferred is about 8.0 percent.

The amount of dispersion promoter provided when an organic pigment is used, as characterized herein, is that amount which alters the surface characteristics of the pigment so that it is more readily dispersed within the resin, plastic, paper making composition or other medium in which it is incorporate. Typically, the amount of the dispersion promoter which is supplied to the organic pigment may be from as little as about 1.00 weight percent to about 15.0 weight percent, based upon the weight of the organic pigment. As a rule, about 4.0 to about 10.0 weight percent of the dispersion promoter and/or its derivatives is adequate for the purposes of appropriately altering the surface characteristic of the pigment. Most preferred is about 4.0 percent.

The amount of dispersion promoter provided when inert pigments are used, as characterized herein, is that amount which alters the surface characteristics of the pigment so that it is more readily dispersed within the resin, plastic, paper making composition or other medium in which it is incorporated. Typically, the amount of the dispersion promoter which is supplied to the inert pigment may be from as little as about 0.25 weight percent to about 3 weight percent of the dispersion promoter and/or its derivatives is adequate for the purposes of appropriately altering the surface characteristic of the pigment. Most preferred is 1%.

The amount of dispersion promoter provided when inorganic color pigments are used, as characterized herein, is that amount which alters the surface characteristics of the pigment so that it is more readily dispersed within the resin, plastic, paper making composition or other medium in which it is incorporated. Typically, the amount of the dispersion promoter which is supplied to the inorganic color pigments may be from as little as about 0.25 weight percent to about 5 weight percent of the dispersion promoter and/or its derivatives is adequate for the purposes of appropriately altering the surface characteristic of the pigment. Most preferred is 2%.

The surfactants of this invention perform the role of dispersants when added directly to conventional paint formulations.

The dispersion promoter and/or its derivatives may be provided on the titanium dioxide particles by any of the known methods by which dispersion promoters are similarly supplied to particulate surfaces. Thus adding the dispersion promoter to the particles while tumbling, mixing the particles in a dilute liquid composition containing the dispersion promoter, or forming a slurry of the particles and dispersion promoter and drying, spray drying or the like represent adequate treating procedures.

The plastics and/or resin in which the titanium dioxide particles treated with the dispersion promoter and/or its derivatives include essentially any plastic and/or resin. Included in the definition of plastic are rubber compounds. The treated titanium dioxide particles may be supplied to the plastic and/or resin while the same is in any liquid or compoundable form such as a solution, suspension, latex, dispersion, and the like. It makes no difference form the standpoint of this invention whether the plastic contains solvent or nonsolvent, or the solvent is organic or inorganic except, of course, it would not be desirable for any plastic or resin or any of the treated titanium dioxide to employ a solvent or dispersing medium which deleteriously affects the components being blended.

Suitable plastics and resins include, by way of example, thermoplastic and thermosetting resins and rubber compounds (including thermoplastic elastomers). The plastics and resins containing the treated particles of this invention may be employed, for example, for molding (including extrusion, injection, calendaring, casting, compression, lamination, and/or transfer molding), coating (including lacquers, film bonding coatings, powder coatings, coatings containing only pigment and resin, and painting,) inks, dyes, tints, impregnations, adhesives, caulks, sealants, rubber goods, and cellular products. Thus the choice and use of the plastics and resins with the treated particles of this invention is essentially limitless. For simple illustration purposes, the plastics and resins may be alkyd resins, oil modified alkyd resins, unsaturated polyesters employed in GRP applications, natural oils, (e.g., linseed, tung, soybean), epoxides, nylons, thermoplastic polyester (e.g., polyethyleneterephthalate, polybutyleneterephthalate), polycarbonates, polyethylenes, polybutylenes, polystyrenes, styrene butadiene copolymers, polypropylenes, ethylene propylene co- and terpolymers, silicone resins and rubbers, EPDM rubbers, SBR rubbers, nitrile rubbers, natural rubbers, acrylics (homopolymer and copolymers of acrylic acid, acrylates, methacrylates, acrylamides, their salts, hydrohalides, etc.), phenolic resins, polyoxymethylene (homopolymers and copolymers), polyurethanes, polysulfones, polysulfide rubbers, nitrocelluloses, vinyl butyrates, vinyls (vinyl chloride and/or vinyl acetate containing polymers) ethyl cellulose, the cellulose acetates and ethylene-vinyl acetate copolymers, ethylene-acrylic acid copolymers, ethylene-acrylate copolymers), and the like.

Most pigments go through an aqueous phase in manufacture in which the pigment particles are present at maximum fineness. This phase offers an ideal opportunity to contact the individual particles with a surface treating agent or surfactant with resulting important benefits to pigment dispersibility. The agents of the present invention are produced from a combination of the following materials described in the general formula:
  a Sulfonic Acid
  a Fatty Acid or a Polymerized Fatty Acid
  a Polyamine, preferably a Diamine
Sulfonic acids used to advantage include methane sulfonic acid, p-toluene sulfonic acid, and dodecylbenzyl sulfonic acid.

Advantageous fatty acids include stearic and oleic acids and polymerized $C_{18}$ fatty acids.

Advantageous diamines include diamines having the general formula $RNH(CH_2)_3NH_2$ where R is an alkyl group and ether diamines having the general formula $RO(CH_2)_3NH(CH_2)3NH_2$ where R is an alkyl group. Fatty triamines and tetramines may also be used. Amines of other configurations such as imidazolines may also be usefully employed.

Particularly good results were achieved through combining one equivalent of methane sulfonic acid and three equivalents of stearic acid with four equivalents of an ether diamine having the formula $RO(CH_2)_3NH(CH_2)_3NH_2$ where R is an alkyl group having eighteen carbon atoms. This formulation may conveniently be designated Formula A. Outstanding pigmentary properties were achieved when Formula A was applied to titanium dioxide which had received no prior surface treatment and Formula A was applied at the rate of one to three percent based on dry weight of pigment. Formula A also produced excellent results with other pigments when slurried with pigment press cakes. Not surprisingly, Formula A also gave excellent results when used as the sole dispersant added to the grind portion of a conventional paint dispersion.

In some instances the advantages provided by the surface treating agents of this invention are enhanced if the pigment particles are first exposed to minute amounts of materials of high charge density which bind to pigment surfaces and then act to attract the surface treating agents and bind them more closely and with more complete coverage to pigment particle surfaces. Strong acids such as methane sulfonic acid and formic acid were found to be effective when used in this manner. Methane sulfonic acid, in the amount of one-tenth of one percent of dry weight of pigment, enhanced the performance of Formula A when added to pigment slurry and mixed prior to adding Formula A. In some instances, depending on the pigment surface in question, strong bases such as 2-amino-2-methyl-1-propanol may be used. Again, depending on the pigment and the formulation being used, the surface treating agent is added to the pigment slurry alone and mixed for optimum pigment particle coverage.

Though this invention has been described in detail, the following examples are provided by way of illustration.

EXAMPLE 1

Titanium Dioxide - Accelerated Exposure (ASTM G53-91)
QUV Weather-Ometer (Atlas UVCON UltraViolet/
Condensation Screening Device) - 500 Hours Coatings were prepared using the following paint formulation:
  173.6 grams medium oil alkyd
   22.0 grams mineral spirits
   59.0 grams pigment
       plus driers and anti-skinning agent
The following pigments were included in tests:
  I. Untreated $TiO_2$ slurry:
      0.2% (on pigment solids) formic acid added and mixed.
      3.0% Formula A (one equivalent methane sulfonic acid, 3 equivalents stearic acid, and 4 equivalents of an ether diamine of the formula $RO(CH_2)_3NH(CH_2)_3NH_2$ where R is an alkyl group having 18 carbon atoms) surface treating agent added and mixed.
      Pigment was dried and dispersed using a high speed disc impeller - no dispersant added.
  II. Untreated $TiO_2$ slurry:
      0.2% (on pigment solids) formic acid added and mixed.
      3.0% (on pigment solids) Formula B (one equivalent methane sulfonic acid plus one equivalent of stearic acid added to two equivalents of ether diamine (as in Formula A) - added and mixed.
      Pigment was dried and dispersed using a high speed disc impeller - no dispersant added.
  III. Titanium dioxide (ASTM 476-73 1988. Type II, III, IV):
      Lecithin was added to the paint formulation.
      Pigment was dispersed using a high speed disc impeller.
  IV. $TiO_2$ untreated slurry:
      Slurry was dried and used with no further treatment.
      Lecithin was added to the paint formulation.
      Pigment was dispersed with steel balls in a mill on a paint shaker.

Steel and aluminum panels were prepared using each of the four dispersions applied at the rate of 8 mils wet. Panels were exposed for 500 hours in a QUV Weather-Ometer. Gloss readings were taken before and after exposure:

| PANEL | 60° INITIAL GLOSS | 60° GLOSS AFTER 500 HOURS |
|---|---|---|
| 1. Steel Formula A | 89 | 76 |
| 2. Steel $TiO_2$ (Type II, III, IV) | 84 | 83 |
| 3. Steel Formula B | 88 | 74 |
| 4. Aluminum Formula A | 86 | 81 |
| 5. Aluminum $TiO_2$ (Type II, III, IV) | 82 | 82 |
| 6. Aluminum Formula B | 89 | 71 |
| 7. Aluminum $TiO_2$ (Untreated Slurry) | 70 | 61 |
| (No steel panel for untreated slurry) | — | — |

EXAMPLE 2

Titanium Dioxide—Exterior Exposure

Formula A, Formula B, and Titanium Dioxide (Type II, III, IV) paint formulations of Example 1 were applied to seven inch sections of a panel of Masonite hardboard 4"×21". Film thickness was 8 mils wet. The films were dried and the panel was exposed 45° South at Laurel, Miss., U.S.A. from May 22, 1996 to Nov. 12, 1996. The painted sections were examined after exposure. No embrittlement, chalking, erosion or other paint film defects were found. Gloss readings were made after exposure with the following results:

|  | 60° Gloss |
|---|---|
| Formula A | 55 |
| Titanium Dioxide (Type II, III, IV) | 52 |
| Formula B | 48 |

EXAMPLE 3

Dispersion of Titanium Dioxide—Direct Addition of Surfactant

Not surprisingly, the surface treating agents of this invention perform as surfactants when used as dispersants in conventional paint formulations.

```
400 ml plastic beaker - 2" blade - 2500 rpm
Grind portion:
    48 grams medium oil alkyd
    96 grams Titanium dioxide
       (95% TiO2—Al2O3 additive - Type II, III, IV as in Example 1)
    2.0 grams Formula A
Grind is almost clean in 2 minutes. 7–8H in 5 minutes.
Add:
    31.85 grams medium oil alkyd
    22.50 grams mineral spirits
          driers and antiskinning agent
Films of resulting paint are smooth, high gloss.
```

EXAMPLE 4

Phthalocyanine Blue—Filter Cake (45% Solids)

Phthalocyanine blue filter cake was treated with 4% (on pigment solids) Formula C (one equivalent of methane sulfonic acid and one equivalent of polymerized $C_{18}$ fatty acid were added to two equivalents of an ether diamine $RO(CH_2)_3NH(CH_2)_3NH_2$ where R is an alkyl group containing 18 carbon atoms). The filter cake was slurried with surface treating agent and dried. The resulting surface treated pigment is suitable for dispersion in both solvent-borne and water-borne inks.

EXAMPLE 5

Aluminum Trihydroxide—Filter Cake (50% Solids)

Aluminum trihydroxide (median particle size 1.0 micron) filter cake was first slurried with 0.2% of acetic acid (by weight on pigment solids) and then surface treated by adding 1.0% Formula D (one equivalent of methane sulfonic acid plus three equivalents of polymerized $C_{18}$ fatty acid were combined with four equivalents of the twenty-four carbon ether diamine of Formula A). The dried pigment is suitable for dispersion in alkyd resin and EPDM rubber formulations.

EXAMPLE 6

Titanium Dioxide—Untreated Slurry (30% Solids)

Methane sulfonic acid, at the rate of 0.1% on pigment solids, was added to untreated titanium dioxide slurry, mixed and heated. Formula A, at the rate of 3.0% on pigment solids, was added, the slurry heated, remixed and dried. The resulting surface treated titanium dioxide pigment is suitable for dispersion in both solvent-borne and water-borne coating formulations.

What is claimed is:

1. A surfactant consisting of the product of the simultaneous reaction of: a Sulfonic Acid, a saturated Fatty Acid and a Polyamine in which the number of amine to acid equivalents is equal.

2. The surfactant of claim 1 wherein the Fatty Acid is a Polymerized Fatty Acid.

3. The surfactant of claim 1 wherein the Polyamine is a Diamine.

4. The surfactant of claim 1 wherein the Fatty acid has from 8 to 54 carbon atoms.

5. The surfactant of claim 4 wherein the Fatty acid has from 12 to 36 carbon atoms.

6. The surfactant of claim 5 wherein the Fatty acid has from 18 to 24 carbon atoms.

7. The surfactant of claim 1 wherein the Polyamine has up to 30 carbon atoms.

8. The surfactant of claim 7 wherein the Polyamine has from 8 to 26 carbon atoms.

9. The surfactant of claim 8 wherein the Polyamine has from 12 to 24 carbon atoms.

10. The surfactant of claim 1 wherein the Sulfonic Acid is selected from the group consisting of aliphatic and aromatic Sulfonic Acids.

11. The surfactant of claim 4 wherein the Fatty acid is Stearic Acid.

12. The surfactant of claim 4 wherein the Fatty acid is Oleic Acid.

13. The surfactant of claim 7 wherein the Polyamine is an Ether Diamine.

14. The surfactant of claim 7 wherein the Polyamine is a Tallow Diamine.

15. The surfactant of claim 7 wherein the Polyamine is a Tallow Triamine.

16. The surfactant of claim 7 wherein the Polyamine is a Tallow Tetraamine.

17. The surfactant of claim 1 wherein the Sulfonic Acid is selected from the group consisting of methane sulfonic acid, p-toluene sulfonic acid, and dodecylbenzene sulfonic acid.

18. The surfactant of claim 1 consisting of the reaction product of 1 equivalent of a Sulfonic Acid, 3 equivalents of a Fatty Acid, and 4 equivalents of an Ether Diamine.

19. The surfactant of claim 1 consisting of the reaction product of 1 equivalent of a Sulfonic Acid, 1 equivalent of a Fatty Acid and 2 equivalents of an Ether Diamine.

20. The surfactant of claim 1 wherein the number of Fatty Acid equivalents and Sulfonic Acid equivalents are equal.

21. The surfactant of claim 1 wherein the number of Fatty Acid equivalents and Sulfonic Acid equivalents are not equal.

* * * * *

UNITED STATES PATENT AND TRADEMARK OFFICE
CERTIFICATE OF CORRECTION

PATENT NO.   : 5,808,118
DATED        : September 15, 1998
INVENTOR(S)  : George Kimball Atkinson It is certified that error appears in the above-identified patent and that said Letters Patent is hereby corrected as shown below:

<u>Column 8,</u>
Line 62, add:

22. A surfactant consisting of the product of the simultaneous reaction of a sulfonic acid, a fatty acid, and a polyamine wherein the amine equivalents contained in the ployamine are equal to the number of acid equivalents contained in the sulfonic acid and the fatty acid combined.

23. The surfactant of claim 22 wherein the fatty acid is unsaturated.

24. The surfactant of claim 22 wherein the number of sulfonic acid equivalents is equal to the number of fatty acid equivalents.

25. The surfactant of claim 22 wherein the number of sulfonic acid equivalents is not equal to the number of fatty acid equivalents.

26. The surfactant of claim 23 wherein the fatty acid is polymerized.

Signed and Sealed this

Twenty-first Day of August, 2001

*Attest:*

*Attesting Officer*

NICHOLAS P. GODICI
*Acting Director of the United States Patent and Trademark Office*